(12) United States Patent
Baud et al.

(10) Patent No.: US 8,604,066 B2
(45) Date of Patent: Dec. 10, 2013

(54) COMPOSITION THAT COMPRISES AT LEAST ONE OXIME AND ITS USE IN THERAPEUTICS

(75) Inventors: Frédéric J. Baud, Montmorency (FR); Pascal Houze, Beauchamp (FR); Maya Kayouka, Paris (FR)

(73) Assignee: SERB, Paris (FR)

( * ) Notice: Subject to any disclaimer, the term of this patent is extended or adjusted under 35 U.S.C. 154(b) by 49 days.

(21) Appl. No.: 13/247,391

(22) Filed: Sep. 28, 2011

(65) Prior Publication Data

US 2012/0041037 A1    Feb. 16, 2012

Related U.S. Application Data

(62) Division of application No. 12/233,620, filed on Sep. 19, 2008, now abandoned.

(60) Provisional application No. 60/973,504, filed on Sep. 19, 2007.

(51) Int. Cl.
*A61K 31/4425* (2006.01)
*A61P 11/00* (2006.01)

(52) U.S. Cl.
USPC .......................................... 514/357; 514/315

(58) Field of Classification Search
USPC .................................................. 514/357, 315
See application file for complete search history.

(56) References Cited

U.S. PATENT DOCUMENTS 7,238,661 B2    7/2007    Glynn

OTHER PUBLICATIONS

Vitarius,"Kinetic Mechanism of the Detoxification of the Organophosphate Paraoxon by Human Serum A-Esterase", Drug Metabolism and Disposition, 22 (3), 1994, pp. 472-478.*
Holstege, "Insecticides", Current Treatment Options in Neurology 2004, 6, pp. 17-23.*
Kayouka et al., "Pralidoxime kinetics in rats pre-treated with organic cationic transporters substrates", Toxicology Letters, Elsevier Biomedical Press, Amsterdam, NL, vol. 164, Sep. 20, 2006, pp. S238-S239, XP005608962.
Josselson J. et al., "Effect of Intravenous Thiamine on Pralidoxime Kinetics", Clinical Pharmacology and Therapeutics, vol. 24, No. 1, 1978, pp. 95-100, XP009096726.
Jeevarathinam K. et al., "Pharmacokinetcs of Pralidoxime Chloride and Its Correlation With Therapeutic Efficacy Against DFP Intoxication in Rats", Die Pharmaie, vol. 43, No. 2, 1988, pp. 114-115, XP001538053.
Jokanovic et al., "Current understanding of the application of pyridinium oximes as cholinesterase reactivators in treatment of organophosphate poisoining", European Journal of Pharmacology, Amsterdam, NL, vol. 553, No. 1-3, Nov. 23, 2006, pp. 10-17, XP005777643.
Kayouka et al., "Does modulation of organic cation transporters improve pralidoxime activity in an animal model of organophosphate poisoning", Crit Care Med 2011, vol. 39, No. 4.
Kayouka et al., "Acute renal failure enhances the antidotal activity of pralidoxime towards paraoxon-induced respiratory toxicity", Toxicology Letters 189 (2009) 48-56.

* cited by examiner

*Primary Examiner* — Sreeni Padmanabhan
*Assistant Examiner* — Sahar Javanmard
(74) *Attorney, Agent, or Firm* — Young & Thompson

(57) ABSTRACT

A medication, a pharmaceutical composition, and method for the treatment of respiratory poisoning in animals and humans caused by organophosphorus compounds, whereby said medication and said pharmaceutical composition comprise at least one oxime and one blocker of organic cation transporters (OCT).

14 Claims, 2 Drawing Sheets

COMPOSITION THAT COMPRISES AT LEAST ONE OXIME AND ITS USE IN THERAPEUTICS

CROSS REFERENCE TO RELATED APPLICATIONS

This application is a division of application Ser. No. 12/233,620 filed on Sep. 19, 2008; which claimed priority from provisional application 60/973,504 filed Sep. 19, 2007. The entire contents of each of the above-identified applications are hereby incorporated by reference.

BACKGROUND OF THE INVENTION

This invention relates to a composition that comprises at least one oxime and its use for the treatment of respiratory poisoning caused by organophosphorus compounds.

DESCRIPTION OF THE RELATED ART

The organophosphates (OP) constitute a big family of chemical compounds that have been synthesized since the 1940's and that have been introduced as highly effective pesticides (P. Taylor, *Anticholinesterase Agents* in: Goodman, A.; Goodman, L. S.; Rall, T. W.; Murad, F. (eds.), The Pharmacological Basis of Therapeutics, 1985, 7th Ed. MacMillan, New York, pp. 100-119). These substances pose a high risk for public health due to the high frequency of poisonings: according to data from the World Health Organization, there are more then 3 million cases of severe poisoning by organophosphorus compounds and more than 220,000 deaths annually (WHO, *Public Health Impact of Pesticides Used in Agriculture*, Geneva 1990; WHO, *Officina Sanitaria Panamericana, Plaguicidas y Salud en las Americas*, Serie Ambiental 12, Washington D.C., 1993; Segura et al., *Arch. Pharmacol.*, 1999, 360: 699-710). The organophosphates that are widely used in agriculture and veterinary medicine as insecticides and antihelminthic compounds are inhibitors of cholinesterases (acetylcholinesterase, butyrylcholinesterase, carboxyesterase). The inhibition of acetylcholinesterase in the central and peripheral nervous tissues causes the accumulation of the cholinergic neuromediator, acetylcholine, at the level of cholinergic synapses, which induces hyperactivation of muscarinic, nicotinic and central receptors followed by their desensitization. The hyperactivation of the postganglionic nicotinic receptors stimulates the neurotransmission in the sympathetic and parasympathetic fibers. The stimulation of the postganglionic muscarinic receptors of the parasympathetic fibers induces the appearance of the muscarinic syndrome (hypersalivation, watering of the eye, sweating, rhinorrhea, bronchorrhea, dyspnea, bronchial spasm, myosis, accommodation paralysis, abdominal pains, vomiting, diarrhea, involuntary urination, hypotension, bradycardia, and auriculoventricular conduction problems). The hyperactivation of the postsynaptic nicotinic receptors at the neuromuscular junction induces the nicotinic syndrome (fasciculations, asthenia, and muscular paralysis). Sympathetic hyperstimulation is responsible for sinus tachycardia, myocardial hyperexcitability, hypertensive episodes and hypokalemia. At the level of the central nervous system, the accumulation of acetylcholine can cause various effects such as anxiety, confusion, speech problems, convulsions, ataxia, and coma (Namba et al. *Am. J. Med.*, 1971, 50: 475-492; T. Namba, *Med. Times*, 1972, 100: 100-126; W. J. Hayes, Jr., *Pesticides Studied in Man*, 1982, Williams and Wilkins, Baltimore, Md., pp. 284-435; D. J. Humphreys, Veterinary Toxicology, 1988, 3rd Ed. Bailliere Tindall, Philadelphia; Landier et al. *Urgences [Emergencies]*, 1995, XIV: 213-215). Certain organophosphorus compounds also bring about the phosphorylation of another type of esterase: the neuropathy target esterase (NTE) (Aldrige and Barnes, *Biochem Pharmacol*, 1966, 15: 549-554), whose inhibition is contemporaneous with a central and peripheral ascending distal axonopathy that takes place two to five weeks after the poisoning (M. B. Abou-Donia, *Science*, 1979, 205: 713-715).

It has been documented that the major cause of death, in the event of severe and acute poisoning by an organophosphorus compound, is due to a respiratory depression of central origin or to a peripheral respiratory insufficiency, resulting from the paralysis of the diaphragm muscle; death may also be due to cardiac arrest (Durham and Hayes, *Arch. Environ Health*, 1962, 5: 27-53; Humphreys, 1988, supra; Lerman and Gutman, *Med. Hypotheses*, 1988, 26: 267-269; M. Yamashita, *Vet. Human Toxicol.*, 1997, 39: 84; Poinsindex, CD-ROM Edition, 2000, Vol. 103, Micromedex). The respiratory problems caused by poisoning with the organophosphorus compounds are highly complex: they are the result of the combination of muscarinic syndromes (bronchial spasms, bronchorrhea), nicotinic syndromes (paresis and paralysis of respiratory muscles) (Lund and Monteagudo, S. Afr. Med., 1986, 69: 6; Dive et al., *Human Exp Toxicol.*, 1994, 13: 271-274; Betrosian et al., *J. Toxicol.—Clin. Toxicol.*, 1995, 33: 257-260; Thompson and Stocks, *Arch. Otolaryngol.— Head Neck Surg.*, 1997, 123: 93-96) and central syndromes (coma with obstructive apnea), whereby the latter is not specific to poisoning but common to all the coma states.

Studies of electrophysiology and histology in vitro have shown that the inhibitors of the cholinesterases depress the diaphragmatic contractility in rats (J. G. Clément, *Eur. J. Pharmacol.*, 1979, 53: 135-141; French et al., *Eur. J. Pharmacol.*, 1983, 91: 399-409; A. P. Smith, *J. Pharm. Pharmacol.*, 1993, 45: 176-181), and certain recent studies even show a partial necrosis of muscular fibers (J. De Bleecker, *J. Toxicol.—Clin. Toxicol.*, 1995, 33: 683-686; Cavaliére et al., *Rev Saude Publica*, 1998, 30: 267-272). In vivo studies in men (De Bleecker 1995, supra) and in rats (De Bleecker et al., *Neurotoxicology*, 1994, 15: 331-340; De Bleecker 1995, supra; Dongren et al., *Toxicol. Letters*, 1999, 107: 249-254) have shown that the late-onset syndromes during poisoning with weakness and paralysis of the upper and lower members are combined with an alteration of the electromyographic parameters of peripheral, muscular fibers. However, there do not exist, to our knowledge, works that have studied the respiratory effects in vivo of an organophosphate poisoning, whereas this device seems to be the essential target of these poisons.

The antidote that is conventionally used against poisoning with organophosphates consists of atroprine. However, the administered doses should be very high and should be repeated for at least 24 hours so that the patient has a reduction of symptoms without the definitive return to a normal state being ensured. The administration of this antidote is systematically combined with measures for decontamination and symptomatic treatments (tracheal incubation, bronchial inhalations and treatment of convulsions, in particular by diazepam).

There is therefore a real need for means for more effective treatment of respiratory poisoning caused by organophosphates that are present in particular in pesticides, and in particular means for allowing patients to recover very quickly and sustainably the respiratory capacity they had before being poisoned.

The filing company, after much research, has had the great advantage of finding that it was possible to improve the recovery of a patient who has been poisoned by organophosphates by blocking the specific organic cation transporters at the renal level of the poisoned patient and by administering to the patient an effective amount of an oxime or a mixture of oximes with preferential renal elimination.

SUMMARY OF THE INVENTION

In this invention, the term "patients" covers human beings and animals. The term "oxime" is used to refer to an oxime or a mixture of oximes with preferential renal elimination. The oxime can be used as such or in the form of its salts and pharmaceutically acceptable hydrates. By way of example of oxime, it is possible to cite in particular pralidoxime, obidoxime, Hi-6 and mixtures thereof. By way of example of pharmaceutically acceptable salts, it is possible to cite methyl sulfate, iodide, chloride, and methanesulfonate. The term "blocking of the OCT [organic cationic transporter]" is used in this description to designate the blocking of specific organic cation transporters at the renal level.

Under pathological conditions, the blocking of the OCT may be due to renal insufficiency of the patient, in which case only oxime is administered to the patient.

The blocking of the OCT can also be caused by the administration of a chemical substance. The blocking of the OCT is then temporary.

The patient who has undergone poisoning caused by organophosphates whose OCT have been blocked and to whom at least one oxime has been administered quickly and sustainably recovers all his respiratory functions.

Thus, the invention relates to the use of at least one oxime in an effective amount for the treatment of the poisoning by organophosphorus compounds of patients whose OCT have been blocked.

The invention relates to the use of at least one oxime for the preparation of a medication that is intended for the treatment of the poisoning of patients whose OCT have been blocked.

The OCT1, 2 and 3 can all be blocked or else at least OCT 1 and 2 are blocked.

The patients whose OCT have been blocked can be patients that have renal insufficiency (pathological conditions) or else patients in whom the blocking of the OCT has been brought about in particular by administration of a chemical agent.

The poisoning suffered by the patients that the invention has as its object to treat is a poisoning caused by organophosphorus compounds (which are referred to in the text either as organophosphorus compounds or organophosphates). These organophosphorus compounds are active substances that are used as pesticides in agriculture. By way of examples of such organophosphorus compounds, it is possible to cite in particular paraoxon, dichlorvos, chlorpyrifos, fenthion, and dimethoate.

According to a particular embodiment of the invention, the administration of oxime and the agent that blocks the OCT can be done sequentially, simultaneously or successively. According to an advantageous embodiment, the administration of the agent blocking the OCT is done before the administration of oxime. The administration of the blocking agent can be done in approximately 60 minutes, preferably approximately 30 minutes, and, more preferably still, approximately 15 minutes before the oxime is administered.

The administration can be done orally or parenterally. The oxime can be administered, for example, by injection, and the agent that blocks the OCT can be administered orally.

The amount of oxime will be determined by the doctor on the basis in particular of weight, the condition of the patient to be treated, the method of administration and/or the extent of the poisoning. In general, a loading dose on the order of 1 to 10, preferably 5 mg/kg of body weight, is administered, then so-called maintenance doses on the order of 20 to 100, preferably 25 to 50 mg/kg of body weight and per day, are administered regularly, for example every hour for 12 to 48 hours.

The amount of agent blocking the OCT will be determined by the doctor on the basis in particular of weight, condition, age, and sex of the patient to be treated as well as the method of administration and the duration of the temporary condition desired.

Another object of the invention is a medication that comprises at least one oxime and at least one agent that blocks the OCT as active ingredients.

This invention also relates to a pharmaceutical composition that comprises at least one oxime and at least one agent that blocks the OCT as active ingredients as well as at least one pharmaceutically acceptable vehicle.

The pharmaceutical composition according to the invention can be administered sequentially, simultaneously or successively and comprises at least one oxime, optionally with at least a first vehicle, and at least one agent that blocks the OCT, optionally with at least a second vehicle, whereby the first vehicle can be identical to the second vehicle.

The selection of the vehicles will be based on the galenical form of the composition.

In particular, if the composition is in the form of a solution for injection, the vehicle will be the physiological solution. The composition according to the invention can also come in a form for oral administration, such as tablets, capsules, syrups, dissolving powder, and gels. The composition for a sequenced or successive administration can come in the form of a solution for injection that contains the oxime that is combined with a tablet (or any other oral form) that contains the agent that blocks the OCT.

Within the scope of all of the embodiments of this invention—in the case of medication, pharmaceutical composition, use or method of treatment—the agent that blocks the OCT is selected from the group that comprises tetraethylammonium (TEA), thiamine and mixtures thereof. Preferably, the oxime is pralidoxime, and the agent that blocks the OCT is tetraethylammonium (TEA). Advantageously, TEA is administered 15 minutes before the administration of the pralidoxime.

BRIEF DESCRIPTION OF THE DRAWINGS

Other aspects, objects, advantages and characteristics of the invention will be presented upon reading the non-limiting description that follows and that describes preferred embodiments of the invention that are provided by means of examples only by reference to FIGS. 1 and 2, which are graphic representations of the respiratory frequency based on time.

EXAMPLES

Example 1

The example was carried out on FVB mice obtained from the Charles River Laboratories (BP0109 69592 L'abresle Cedex) and on FVB KO (knock-out) mice for the genes coding for the OCT 1 and 2 that were obtained ex gratia from Dr. Cisternino, member of the Inserm U705. The KO mice strains for the receptors OCT1 and OCT2 are kept at the central breeding lab of the Pharmaceutical Department, Paris V.

The OCT of the KO mice are not expressed.

Three groups of five FVB mice and three groups of five KO mice were determined
Group 1: Control group
Group 2: At time t0, 0.47 mg/kg of paraoxon (PO) was injected subcutaneously into each mouse
Group 3: At time t0, 0.47 mg/kg of paraoxon (PO) was injected subcutaneously into each mouse, and at time t=30 minutes, 50 mg/kg of pralidoxime (PRX) methyl sulfate was injected intramuscularly into them.

The respiratory frequency was measured by full-body plethysmography using a device whose description follows.

The device consists of two Plexiglas chambers, each with a 2.8 liter capacity. The animal is placed in one chamber, while the other chamber is used as a reference. The box that holds the animal is pierced by one opening for admitting compressed air that arrives at 5 L/minute and another opening for air discharge, a thermometer, and a 1 ml syringe that is necessary for calibration. The two boxes are connected to one another:

On the one hand, by a pressure differential sensor (Validyne MP, 45+/−3 cm of $H_2O$, Northridge, Calif.) connected to an integrator that transforms the pressure variation into an electrical signal. This electrical signal is displayed on the computer screen in the form of a plot in a reference whose axis of the abscissas represents time and whose axis of the ordinates represents the electrical signal ranging from −6000 to +6000 millivolts (mV).

On the other hand, by a pipe that has a tight constriction; it allows the slow equilibration of temperatures and pressures without interfering with the signal during recording.

The analysis of the respiratory parameters has been carried out based on plethysmography recordings by using Acquis 1 software (Institut Alfred FRESSARD, CNRS, Gif-sur-Yvette).

Figure 1:
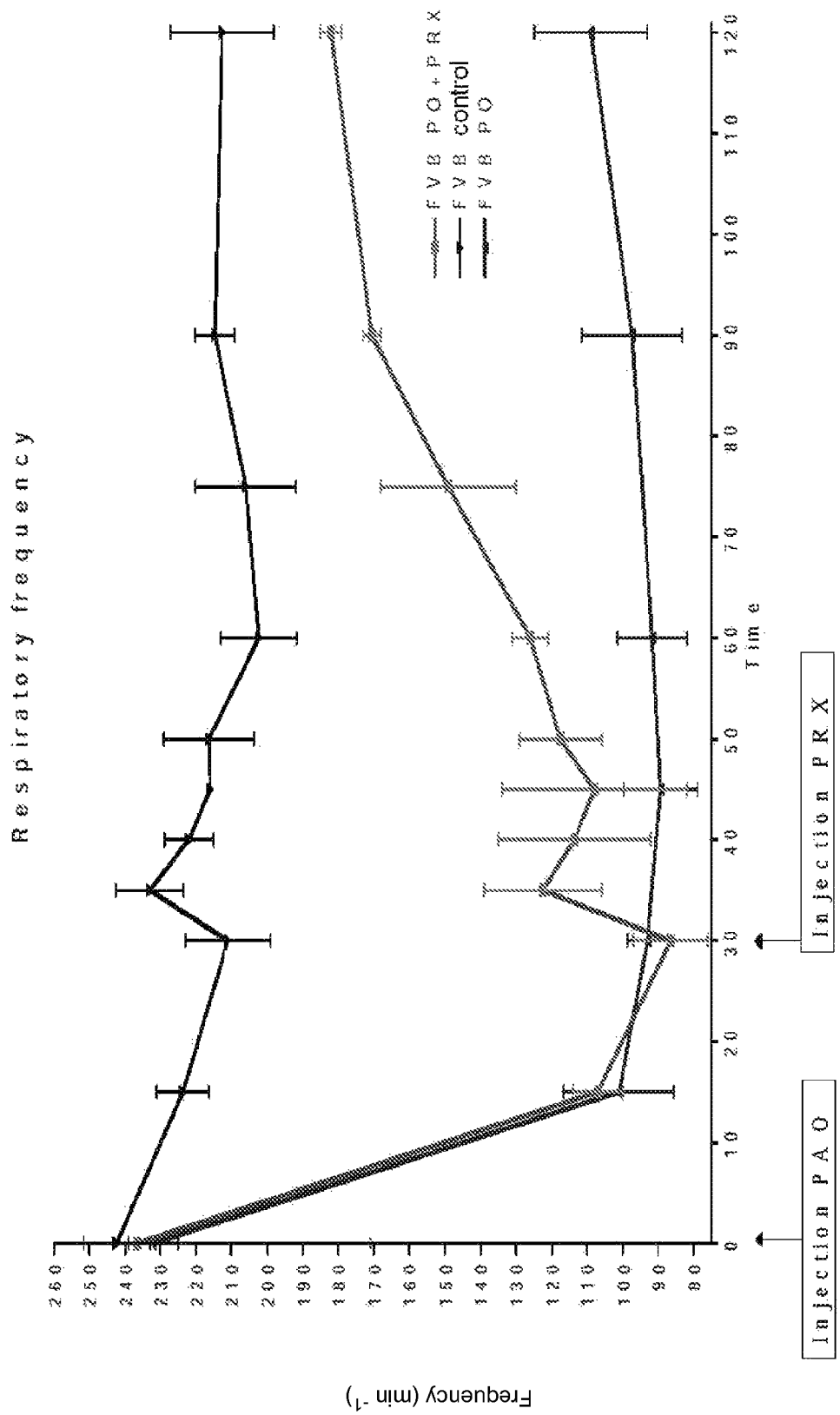
Figure 2:
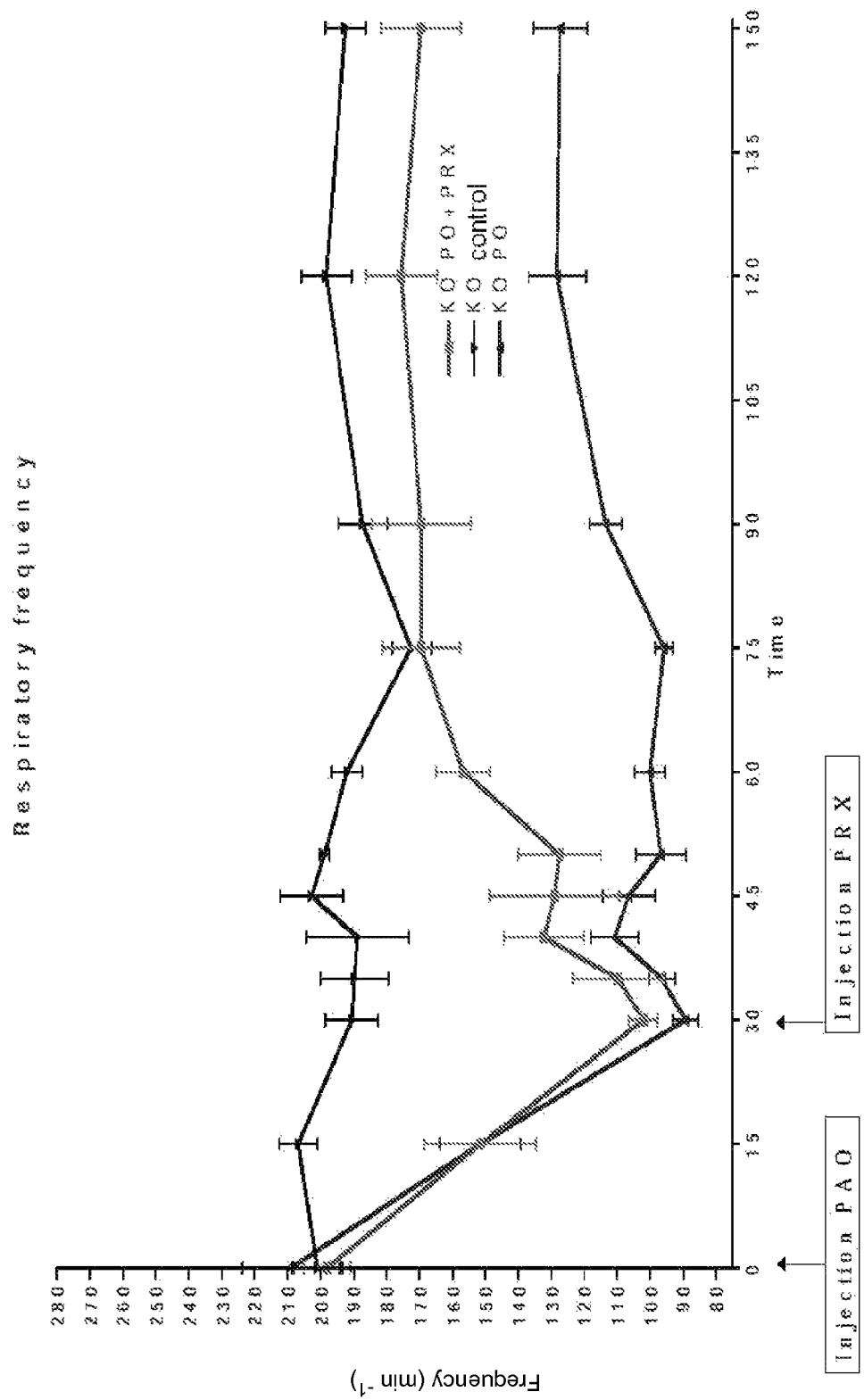

The results of these measurements are presented in FIGS. 1 and 2, which show the respiratory frequency ($min^{-1}$) based on the time in minutes.

These figures show that the correction of the respiratory frequency in KO mice that is obtained after a single injection of PRX is almost complete at time 70 minutes and continues throughout the entire duration of the observation.

The activity of the pralidoxime is therefore extended when the OCT are blocked.

The blocking of the OCT allows for a modulation of the antidotic effect of the pralidoxime.

The invention claimed is:

1. A method for the treatment of respiratory poisoning in animals and humans caused by organophosphorus compounds, comprising:
   blocking of organic cation transporters at the renal level (OCT); and
   administering an effective amount of at least one oxime to an animal or human in need thereof.

2. The method according to claim 1, wherein the blocking of the OCT is due to a renal insufficiency or administration of a chemical agent.

3. The method according to claim 1, wherein the poisoning has been caused by active pesticide substances selected from the group consisting of paraoxon, dichlorvos, chlorpyrifos, fenthion, dimethoate, and mixtures thereof.

4. The method according to claim 2, wherein,
   the blocking of the OCT is due to administration of a chemical agent, and
   the administration of the oxime and the chemical agent that blocks the OCT is sequential, simultaneous or successive.

5. The method according to claim 4, wherein the administration of the chemical agent that blocks the OCT is done approximately 60 minutes before the administration of the oxime.

6. The method according to claim 1, wherein the administration is oral or parenteral.

7. The method according to claim 2, wherein the chemical agent that blocks the OCT is tetraethylammonium (TEA).

8. The method according to claim 7, wherein the oxime is pralidoxime or one of its pharmaceutically acceptable salts.

9. The method according to claim 4, wherein the administration of the chemical agent that blocks the OCT is done before the administration of the oxime.

10. The method according to claim 5, wherein the administration of the chemical agent that blocks the OCT is done approximately 30 minutes before the administration of the oxime.

11. The method according to claim 5, wherein the administration of the chemical agent that blocks the OCT is done approximately 15 minutes before the administration of the oxime.

12. The method according to claim 8, wherein the pharmaceutically acceptable salt is methyl sulfate.

13. The method according to claim 1, wherein the oxime is pralidoxime, obidoxime, Hi-6 or mixtures thereof.

14. The method according to claim 1, wherein the oxime is pralidoxime.

* * * * *